(12) United States Patent
Logan

(10) Patent No.: US 6,280,186 B1
(45) Date of Patent: Aug. 28, 2001

(54) CURVED ELASTOMERIC ORTHODONTIC LIGATURE

(76) Inventor: Lee R. Logan, 4830 Encino Ave., Encino, CA (US) 91316

(*) Notice: Subject to any disclaimer, the term of this patent is extended or adjusted under 35 U.S.C. 154(b) by 0 days.

(21) Appl. No.: 09/605,583

(22) Filed: Jun. 28, 2000

(51) Int. Cl.$^7$ .................................................. A61C 3/00
(52) U.S. Cl. ................................. 433/11; 433/15; 433/18
(58) Field of Search ................................ 433/11, 15, 18

(56) References Cited

U.S. PATENT DOCUMENTS

| | | | |
|---|---|---|---|
| 3,530,583 | 9/1970 | Klein et al. | 433/11 |
| 3,758,947 | 9/1973 | Kesling | 433/18 |
| 3,879,850 | 4/1975 | Wallshein | 433/18 |
| 3,903,601 | 9/1975 | Anderson et al. | 433/3 |
| 3,913,228 | 10/1975 | Wallshein | 433/18 |
| 4,054,997 | 10/1977 | Wallshein | 433/11 |
| 4,127,940 | 12/1978 | Shilliday | 433/3 |
| 4,217,686 | 8/1980 | Dragan | 29/413 |
| 4,330,271 | 5/1982 | Anderson | 433/3 |
| 4,340,363 | 7/1982 | Klein et al. | 433/18 |
| 4,412,820 | 11/1983 | Brummond et al. | 433/18 |
| 4,522,590 | * 6/1985 | Pletcher | 433/15 |
| 4,900,250 | 2/1990 | Kesling et al. | 433/11 |
| 4,946,385 | 8/1990 | Eckert et al. | 433/2 |
| 4,946,386 | 8/1990 | Kidd et al. | 433/18 |
| 4,950,158 | 8/1990 | Barngrover et al. | 433/11 |
| 5,044,946 | 9/1991 | Cleary | 433/18 |
| 5,221,033 | 6/1993 | Klein et al. | 225/52 |
| 5,273,426 | 12/1993 | Dragan | 433/18 |
| 5,317,074 | 5/1994 | Hammar et al. | 528/44 |
| 5,461,133 | 10/1995 | Hammar et al. | 528/10 |
| 5,738,512 | 4/1998 | Cho | 433/3 |
| 5,829,974 | 11/1998 | Brosius | 433/15 |

* cited by examiner

*Primary Examiner*—John J. Wilson
(74) *Attorney, Agent, or Firm*—Christie, Parker & Hale, LLP

(57) ABSTRACT

An elastomeric orthodontic ligature for engagement with a tooth-mounted orthodontic appliance such as a bracket having conventional tie wings. In one application, the ligature is engaged behind and between upper and lower tie wings of the bracket, and extends over the bracket surface to hold an archwire in a slot of the bracket. The ligature differs from known elastic ligatures of flat torus shape in that it is arched or curved to simplify and speed initial engagement behind one of the bracket tie wings.

8 Claims, 1 Drawing Sheet

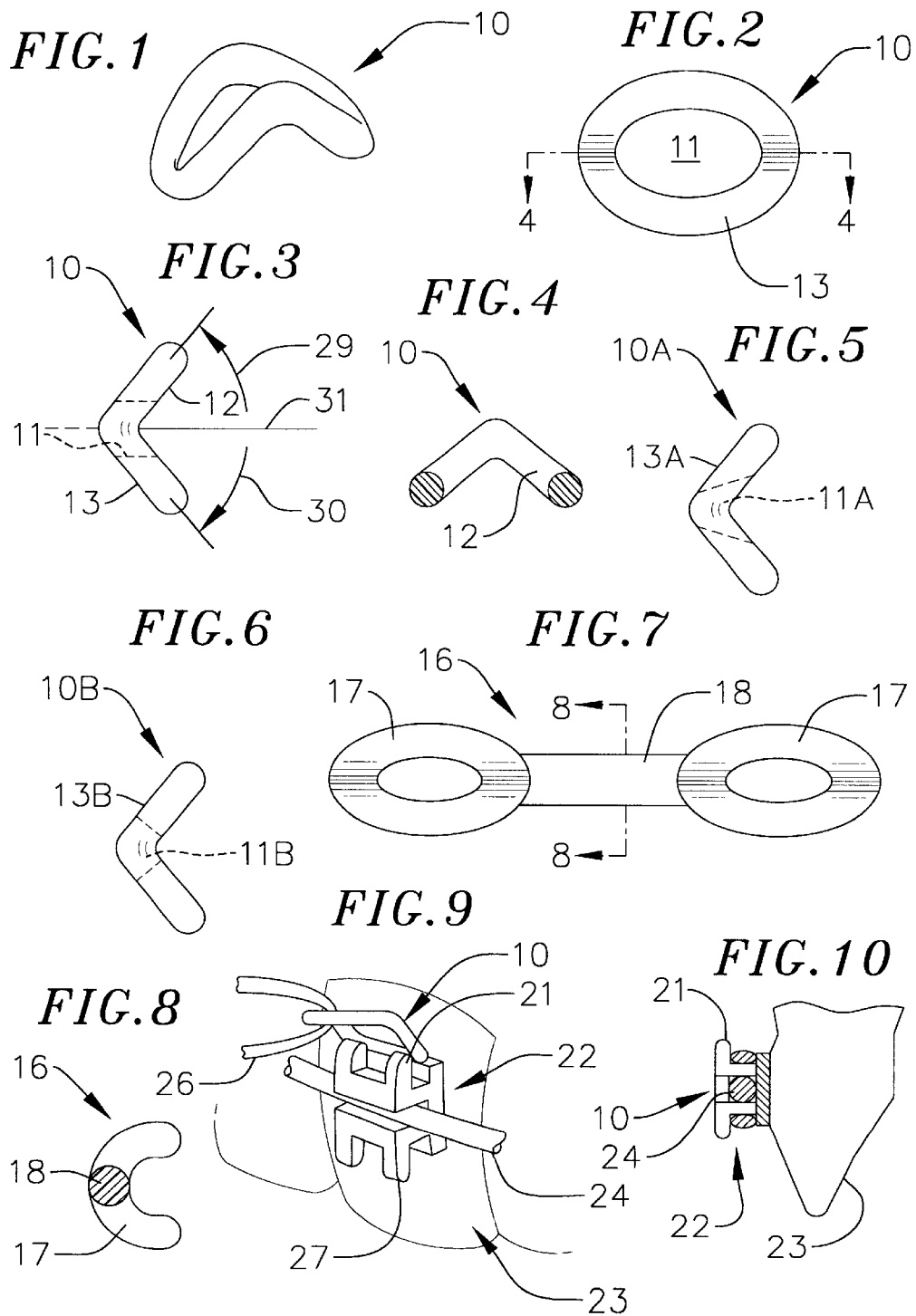

CURVED ELASTOMERIC ORTHODONTIC LIGATURE

BACKGROUND OF THE INVENTION

Orthodontic treatment of improperly positioned teeth involves the application of mechanical forces to urge the teeth of one or both dental arches into an alignment which provides correct occlusion and is cosmetically attractive. Most techniques use so-called orthodontic brackets which are small slotted metal or ceramic bodies shaped for direct cemented attachment to the front or rear surfaces of teeth, or alternatively for attachment to bands which are fitted over and cemented to the teeth.

Most orthodontic brackets in current use are of an "edgewise" style as invented by Edward Angle in the 1920's. An edgewise bracket has a generally mesiodistally extending slot which opens away from the tooth surface on which the bracket is mounted, and is typically rectangular in cross section. A resilient curved archwire is seated in the bracket slot, and the wire is bent or twisted before installation so the resulting restoring force exerted by the seated archwire tends to shift, rotate or tip the associated tooth into a corrected position.

The archwire must be somehow secured in the bracket slot to resist dislodging forces as imposed, for example, during brushing of teeth or chewing of food, or by the restoring force of the archwire itself. The bracket is formed with oppositely extending tie wings, around which some form of ligature can be fastened to extend over the seated archwire to hold it against movement out of the slot. Historically, small stainless-steel tie-wire ligatures have been used, and the installation and anchoring twisting of these tie wires is time consuming, sometimes uncomfortable for the patient, and requires considerable skill.

An important improvement in ligation was made in the 1960's by Drs. Anderson and Klein, and is described in U.S. Pat. No. 3,530,583, the disclosure of which is incorporated herein by reference. The improvement is a torus or doughnut-shaped flat ring of circular cross section, and made of an elastomeric polymer such as polyurethane which is compatible with the environment of the mouth. The ring is stretched over the opposed tie wings, and extends over and against the seated archwire. The elastomeric ligature is generally easier and quicker to install than a wire ligature, and twisting of the wire ends (along with the risk of long-term tissue irritation) is of course eliminated. Flat toroidal rings of this type, and of noncircular cross section, have also been proposed (e.g., U.S. Pat. No. 3,758,947).

Elastic ligatures nevertheless remain a challenge to install, as they must be angled upwardly or downwardly to be hooked over and behind the first tie wing (or an elastic hook if the bracket is so equipped) and similarly maneuvered to fit over and seat behind the opposed tie wing. Just as with wire ligatures, installation on posterior brackets is particularly difficult, and even the anterior brackets are awkward to engage due to interference with the patient's lips or gum tissue by tweezers or forceps which grip the ring during installation.

The problem is compounded by a periodic need to remove and reinstall the ligatures when an archwire is changed or requires adjustment, or when the ligatures lose elasticity and restoring force, or become discolored. Elastic ligatures have also been made available in different colors which are appealing to younger patients, and sometimes ligatures are changed for "vanity" reasons when a child wants different colors. Every ligature change, for whatever reason, includes significant chair time, possible patient discomfort, and the time and attention of the orthodontist and assistants. It is to the solution of these ongoing problems that the present invention is directed.

SUMMARY OF THE INVENTION

The orthodontic ligature of this invention is an arched non-planar ring or loop with a central opening, and which is made of an elastomeric polymer such as polyurethane which is molded in the arched shape. In one form, the ring is folded in a V-shape when viewed from the side. In an alternative form, the ring cross section is substantially constant and circular, and the ring has inner and outer side surfaces which are generally C-shaped and are substantially concentric. Importantly, the arch or fold of the ligature is in the ring itself to avoid projections or tabs which can cause tissue irritation and other problems. de

BRIEF DESCRIPTION OF THE DRAWINGS

FIG. 1 is a perspective view of a arched elastomeric orthodontic ligature according to the invention;

FIG. 2 is a front elevation of the ligature;

FIG. 3 is a side view of the ligature;

FIG. 4 is a sectional view on lines 4–4 of FIG. 2;

FIG. 5 is a side view similar to FIG. 3, but showing an alternative outwardly flared center opening;

FIG. 6 is similar to FIG. 5, but showing an inwardly flared center opening;

FIG. 7 is a front elevation of a double ligature for applying tension force between two anchor points;

FIG. 8 is a sectional view on lines 8–8 of FIG. 7;

FIG. 9 is a perspective view of an orthodontic bracket on tooth, and showing a ligature of the invention positioned for initial engagement; and FIG. 10 is a sectional side view of the bracket shown in FIG. 9 with the ligature fully engaged.

DETAILED DESCRIPTION OF THE INVENTION

An orthodontic ligature 10 according to the invention is shown in FIGS. 1–4. The ligature is an arched, folded continuous ring or loop with a central opening 11, and inner and outer side surfaces 12 and 13 which are non-planar. The ligature is preferably molded in the shape shown in an elastomeric polymer such as polyurethane which is compatible with the environment of the mouth. A number of suitable alternative materials are described in U.S. Pat. No. 5,317,074, the disclosure of which is incorporated herein by reference.

In the embodiment shown in FIGS. 1–4, central opening 11 is oval, but shape variations can easily be made to accommodate different styles of orthodontic brackets or other anchoring devices. For example, FIG. 5 illustrates a ligature 10A with a central opening 11A which decreases in diameter toward outer surface 13A, and FIG. 6 shows a ligature 10B with an oppositely tapered opening 11B. Because the ring is molded, the central opening may also be circular, or any other desired shape. The edges of the hole may also be beveled for easier installation on specific styles of brackets.

In one form, the ligature has a constant circular cross section as shown in FIG. 4, but other or variable cross-sectional shapes can also be used to accommodate different bracket and tiewing shapes, to minimize stress concentrations when stretched, and to vary the elastic properties of the ligature. Similarly, the inner and outer surfaces of the ligature are typically generally parallel as shown in FIG. 3, but other curvatures or angled bends can also be used.

FIGS. 7 and 8 show a double ligature 16 with a pair of spaced-apart arched continuous rings 17 generally as described above, and which are connected by a strand 18 which is integrally molded with the rings. In this embodiment, the rings are C-shaped in side view, and the inner and outer surfaces are substantially concentric. Apart from the arched rings, ligature 16 is similar in function to a corresponding double ligature shown in the aforementioned U.S. Pat. No. 3,530,583 for either inter-arch or intra-arch applications, and in use, strand 18 is tensioned to apply a force urging together spaced-apart brackets or similar anchor points engaged with the rings.

FIG. 9 illustrates the initial installation position of a ligature 10 behind an upper tie wing 21 of an orthodontic bracket 22 secured to a tooth 23. The bracket has a mesio-distal slot in which is seated a portion of an archwire 24 which extends around the patient's dental arch. The archwire is illustrated with a circular cross section, but rectangular or other cross-sectional shapes are in common use. The ligature is gripped by a forceps or tweezer 26 which is moved toward the tooth, and then slightly downwardly to position the leading edge of the ligature behind the tie wing. The gripped end of the ligature is next moved downwardly over the archwire, and then toward the tooth so the gripped end of the elongated and tensioned ligature can be snapped in place behind a lower tie wing 27 of the bracket. A side view of the thus-installed ligature is shown in FIG. 10.

Importantly, the arched shape of the ligature enables the gripping forceps to be moved toward the tooth without uncomfortable interference with the gum, lip or cheek tissue during initial engagement. Ligature installation is accordingly quicker and easier, and with a much lower risk of patient discomfort.

The dimensions of the ligature can be varied as necessary to be compatible with brackets or other anchoring devices of varying shape and size. A typical ligature for tying a rectangular archwire to a single-wing or twin orthodontic bracket will have an outside diameter (as measured along a central horizontal axis of FIG. 2) in the general range of about 0.090 to 0.125 inch, and the diameter of central opening 11 is in the general range of about 0.030 to 0.050 inch. A typical cross-sectional diameter of a ring of this type is about 0.03 to 0.04 inch. The term "ring" is used herein in the sense of a continuous loop which is not necessarily circular, and is more typically noncircular when viewed in front elevation as in FIG. 2.

Referring again to FIG. 2 which is an arched-toroid embodiment of the invention, inner and outer side surfaces 12 and 13 are generally parallel, and the ligature ends define generally equal angles 29 and 30 with respect to a central axis 31 of opening 11. In a typical form compatible with many brackets, angles 29 and 30 are each in the range of about 45 degrees to 75 degrees.

There has been described a new arched continuous-loop elastic ligature which is much easier and faster to install than conventional flat torus-shaped ligatures, and provides significantly improved patient comfort during installation.

What is claimed is:

1. An orthodontic ligature molded from an elastomeric polymer which is compatible with an environment of a patient's mouth, and which in its unstreches is a continuous arched, nonplanar ring having a central opening so it can be engaged with and stretched over an orthodontic appliance on a tooth.

2. The ligature defined in claim 1 in which the ring has a substantially constant cross section.

3. The ligature defined in claim 1 in which the ring cross section is substantially circular.

4. The ligature defined in claim 1 in which the ring is made of polyurethane.

5. The ligature defined in claim 1 in which the ligature has inner and outer surfaces which are generally parallel and V-shaped.

6. The ligature defined in claim 1 in which the ligature has inner and outer side surfaces which are generally C-shaped.

7. The ligature defined in claim 6 in which the inner and outer side surfaces are generally concentric.

8. The ligature defined in claim 1, and further comprising a second continuous arched and nonplanar ring with a central opening, the two rings being spaced apart and joined by an elastomeric strand, the rings and strand being integrally molded of an elastomeric polymer.

* * * * *

UNITED STATES PATENT AND TRADEMARK OFFICE
CERTIFICATE OF CORRECTION

PATENT NO. : 6,280,186 B1
DATED : August 28, 2001
INVENTOR(S) : Lee R. Logan

It is certified that error appears in the above-identified patent and that said Letters Patent is hereby corrected as shown below:

<u>Column 4,</u>
Line 22, replace "in its unstreches" with -- in its unstretched state --.

Signed and Sealed this

Second Day of April, 2002

Attest:

JAMES E. ROGAN
*Attesting Officer*  *Director of the United States Patent and Trademark Office*